(12) United States Patent
Baker et al.

(10) Patent No.: US 7,053,024 B2
(45) Date of Patent: *May 30, 2006

(54) PROCESS FOR MAKING A CATALYST

(75) Inventors: Michael James Baker, Feltham (GB); John William Couves, High Wycombe (GB); Kenneth George Griffin, Royston (GB); Peter Johnston, Royston (GB); James Colin McNicol, Pinner (GB); George Frederick Salem, Naperville, IL (US)

(73) Assignees: BP Chemicals Limited, London (GB); Johnson Matthey Public Limited Company, London (GB)

( * ) Notice: Subject to any disclaimer, the term of this patent is extended or adjusted under 35 U.S.C. 154(b) by 175 days.

This patent is subject to a terminal disclaimer.

(21) Appl. No.: 10/338,673

(22) Filed: Jan. 9, 2003

(65) Prior Publication Data

US 2003/0144544 A1 Jul. 31, 2003

Related U.S. Application Data

(62) Division of application No. 09/626,156, filed on Jul. 26, 2000, now Pat. No. 6,534,438.

(51) Int. Cl.
*B01J 23/00* (2006.01)

(52) U.S. Cl. ...................... 502/439; 502/339
(58) Field of Classification Search ............... 502/439, 502/325, 327–339, 527.12, 527.13, 245, 502/252, 257–262; 560/245
See application file for complete search history.

(56) References Cited

U.S. PATENT DOCUMENTS

| 3,627,821 | A | * | 12/1971 | Sennewald et al. ..... 260/497 A |
| 3,743,607 | A | | 7/1973 | Sennewald |
| 3,761,513 | A | * | 9/1973 | Sennewald et al. ......... 260/497 |
| 3,775,342 | A | | 11/1973 | Kronig et al. |
| 3,855,280 | A | * | 12/1974 | Severs, Jr. ............... 260/497 A |
| 4,048,096 | A | | 9/1977 | Bissot |
| 4,158,737 | A | * | 6/1979 | Bartsch ....................... 560/245 |
| 4,495,308 | A | | 1/1985 | Gibson ....................... 502/355 |
| 4,558,023 | A | * | 12/1985 | Brun et al. ................. 502/108 |
| 4,677,084 | A | | 6/1987 | Bergna |
| 5,179,056 | A | | 1/1993 | Bartley ....................... 502/170 |
| 5,179,057 | A | * | 1/1993 | Bartley ....................... 502/170 |
| 5,185,308 | A | | 2/1993 | Bartley et al. .............. 502/170 |
| 5,189,004 | A | | 2/1993 | Bartley ....................... 502/170 |
| 5,342,987 | A | * | 8/1994 | Bartley ....................... 560/245 |
| 5,347,046 | A | * | 9/1994 | White et al. ................ 560/245 |
| 5,466,652 | A | | 11/1995 | Paparizos et al. |
| 5,559,071 | A | | 9/1996 | Abel et al. .................. 502/326 |
| 5,567,839 | A | | 10/1996 | Gulliver et al. ............ 560/245 |
| 5,571,771 | A | | 11/1996 | Abel et al. .................. 502/330 |
| 5,591,688 | A | | 1/1997 | Blum et al. |
| 5,665,667 | A | | 9/1997 | Lemanski et al. .......... 502/300 |
| 5,674,800 | A | | 10/1997 | Abel et al. .................. 502/326 |
| 5,705,679 | A | | 1/1998 | Nicolau et al. ............. 560/245 |
| 5,808,136 | A | * | 9/1998 | Tacke et al. ................ 560/243 |
| 5,817,866 | A | * | 10/1998 | Bristow et al. ............. 560/245 |
| 6,040,474 | A | * | 3/2000 | Jobson et al. .............. 560/243 |
| 6,268,522 | B1 | | 7/2001 | Hagemeyer et al. ........ 560/245 |
| 6,303,536 | B1 | | 10/2001 | Chen et al. ................. 502/325 |
| 6,342,628 | B1 | * | 1/2002 | Williams et al. ........... 560/245 |
| 6,350,901 | B1 | * | 2/2002 | Kitchen et al. ............. 560/245 |
| 6,376,706 | B1 | * | 4/2002 | Kitchen et al. ............. 560/241 |

FOREIGN PATENT DOCUMENTS

| EP | 0 569 624 A1 | 11/1993 |
| EP | WO 97/36678 | 10/1997 |
| GB | 1 500 167 | 2/1978 |
| GB | 1 521 652 | 8/1978 |
| WO | 99/62632 | 12/1999 |

* cited by examiner

Primary Examiner—Edward M. Johnson
(74) Attorney, Agent, or Firm—Nixon & Vanderhye

(57) ABSTRACT

Process for preparing a supported metal catalyst composition comprising impregnating support particles having a mean diameter of greater than 300 microns with a solution of least one catalytically active metal, or precursor thereof, such that the metal, or its precursor, is in a mobile state in the support particles; and drying the impregnated support particles. The mobile metal, or its precursor, in the support particles is then treated with a liquid comprising at least one reducing agent to deposit and immobilize the metal, or its precursor, in the support particles such that the metal, or its precursor, is distributed in the support particle in a layer below the surface of the support particle, the layer being between an inner and an outer region, each of the inner and outer regions having a lower concentration of the metal or precursor than the layer.

23 Claims, 2 Drawing Sheets

PROCESS FOR MAKING A CATALYST

This application is a Divisional of Application Ser. No. 09/626,156, filed Jul. 26, 2000 now U.S. Pat. No. 6,534,438, the entire content of which is hereby incorporated by reference in this application.

The present invention relates to a metal catalyst composition and in particular to a supported metal catalyst composition. The present invention also relates to a process for making such a catalyst composition

BACKGROUND OF THE INVENTION

Supported metal catalysts are typically made by impregnating a suitable support material with a catalytically active metal or with its precursor. For example, catalysts for use in the production vinyl acetate monomer (VAM) by the reaction of ethylene, acetic acid and oxygen are made by impregnating a support such as silica or alumina with a compound of a Group VIII noble metal such as palladium together with a gold compound and an alkali metal salt, typically in the form of an acetate, the palladium and gold compounds being converted to catalytically active state.

In early examples of fixed-bed catalysts for use in the production of VAM, palladium and gold were distributed more or less uniformly throughout the support, for example, U.S. Pat. No. 3,743,607. Since gaseous reactants do not diffuse significantly into the large fixed-bed catalyst particles, much of the expensive catalytic metal components in the interior of the catalyst were not useful. Subsequently, shell-impregnated, fixed-bed catalysts were developed in which most of the catalytic metals were deposited onto an outer shell of the support particle. For example, Great Britain Patent No. 1,500,167 describes a catalyst in which at least ninety percent of the palladium and gold is distributed in that part of the support particle which is not more than thirty percent of the particle radius from the surface. The palladium and gold being at/near the surface are susceptible to loss through attrition.

In the preparation of shell-impregnated, fixed bed catalysts such as that described in GB 1,500,167 and EP-A-0 569 624, after impregnation of a support with a Group VIII noble metal solution, the noble metal is subsequently precipitated to the support by, for example, treatment with an aqueous solution of an alkali metal salt Such precipitated noble metal has limited mobility.

U.S. Pat. No. 4,677,084 describes a process for preparing attrition resistant catalyst, catalyst precursor and catalyst support particles and in particular silica-containing vanadium/phosphorus oxide catalysts. The catalyst, catalyst precursor or catalyst support particles are slurried in a solution of an oxide such as silica. The slurry is then spray-dried and calcined to produce microspheres. The process results in the formation of an oxide-rich layer at the periphery of each calcined microsphere.

There remains a need for an improved metal catalyst composition and in particular, a supported metal catalyst composition.

SUMMARY OF THE INVENTION

Thus, according to the present invention there is provided a catalyst composition comprising support particles having at least one catalytically active metal distributed therein, in which the metal is distributed in the support particle in a layer below the surface of said particle, said layer being between an inner and an outer region of said support particle, and each of said inner and outer regions having a lower concentration of said metal than said layer.

The catalyst composition can provide high attrition resistance as well as high activity. The outer region of the catalyst composition may also provide some resistance to poisoning of the catalytically active metal.

The present invention also provides a process for preparing a supported metal catalyst composition which process comprises impregnating support particles with a solution of least one catalytically active metal, or precursor thereof, such that the metal, or its precursor, is in a mobile state in the support particles and then treating the mobile metal, or precursor, in the support particles with at least one chemical reagent to deposit and immobilize the metal, or its precursor, in the support particles such that the metal, or its precursor, is distributed in the support particle in a layer below the surface of said support particle, said layer being between an inner and an outer region, each of said inner and outer regions having a lower concentration of said metal or precursor than said layer.

Also, according to the present invention there is provided a composition comprising support particles having at least one precursor of a catalytically active metal distributed therein, in which the precursor is distributed in the support particle in a layer below the surface of said particle, said layer being between an inner and an outer region of said support particle, and each of said inner and outer regions having a lower concentration of said precursor than said layer.

An advantage of the process of the present invention is that by treating a catalytically active metal, or its precursor, which is in a mobile state in the support particle with at least one chemical reagent which deposits and immobilizes it, the metal, or its precursor, is distributed predominantly in a layer below the surface of the particle such that the catalyst composition so produced has high attrition resistance as well as high activity.

Preferably, the concentration of catalytically active metal or of its precursor in each of the inner and outer regions is less than half the concentration of the catalytically active metal or of its precursor in the layer.

In a preferred embodiment, the layer containing the catalytically active metal, or its precursor, has an outer edge which is at least 3% and no more than 75% of the particle radius from the surface of the support particle and preferably, at least 5%, and more preferably at least 10% of the particle radius from the surface of the support particle.

Depending upon the size of the support particles, alternatively or additionally, the layer containing the catalytically active metal, or its precursor, preferably has an outer edge which is at least 3 microns and no more than 20 microns below the surface of each support particle, and is more preferably 4 to 20 microns,below the surface of each particle, and yet more preferably is 5 to 15 microns below the surface of each particle.

Typically, the layer has an average thickness which is less than half the radius of the particle, for example less than 25 microns. Preferably, the layer has an average thickness of greater than 0.1 microns.

The process for preparing the catalyst composition of the present invention may be used for the preparation of catalysts for use in fixed bed or preferably, fluid bed processes, for example, for the production of vinyl acetate monomer A suitable support material for use in a fluid bed process is a microspheroidal particulate material. When the catalyst composition is to be used in a fluid bed process, as is well known in the fluid bed art, the support particles must be small enough to be maintained in a fluid bed state under reaction conditions while keeping sufficient attrition resistance such that excessive amounts of catalyst composition need not be replenished during the process. Further, although typical particle sizes (as measured by mean particle diameters) should not be so large as to be difficult to keep in a fluid bed state, there should not be an excessive amount of very small particles (fines) which are difficult to remove from the system and may plug gas recycle lines. Thus, typically suitable fluid bed support particles have a distribution of larger to smaller particle sizes.

For example, in the fluid bed manufacture of vinyl acetate from ethylene, acetic acid and oxygen-containing gas, typically, at least 80% and preferably at least 90% of the support particles have mean diameters of less than about 300 microns.

A typical catalyst useful in this invention may have the following particle size distribution.

| | |
|---|---|
| 0 to 20 microns | 0–30 wt % |
| 20 to 44 microns | 0–60 wt % |
| 44 to 88 microns | 10–80 wt % |
| 88 to 106 microns | 0–80 wt % |
| >106 microns | 0–40 wt % |
| >300 microns | 0–5 wt % |

Persons skilled in the art will recognize that support particles sizes of 44, 88, and 300 microns are arbitrary measures in that they are based on standard sieve sizes. Particle sizes and particle size distributions may be measured by an automated laser device such as a Microtrac X100.

Microspheroidal support particles useful in the present invention are sufficiently porous to permit gaseous reactants to diffuse into the particle and contact catalytic sites incorporated within the particle. Thus, the pore volume should be high enough to permit gaseous diffusion. However, a support particle with an exceedingly high pore volume typically will not have sufficient attrition resistance or will not have sufficient surface area for catalytic activity. A typically suitable microspheroidal support particle has a pore volume (measured by nitrogen sorption) between about 0.2 and 0.7 cc/g. A preferable support particle has a pore volume between about 0.3 and 0.65 cc/g and more preferably between about 0.4 and 0.55 cc/g.

Surface areas (measured by nitrogen BET) for fluid bed support particles with mean diameters and pore volumes useful in the present invention typically are above about 50 $m^2/g$ and may range up to about 200 $m^2/g$. A typical measured surface area is about 60 to about 125 $m^2/g$.

Typically useful support particles, especially silica support particles are described in U.S. Pat. No. 5,591,688, incorporated by reference herein. In these supports microspheroidal particles are produced by spray drying a mixture of a silica sol with silica particles followed by drying and calcining. In the preparation, at least 10 wt. %, preferably at least 50 wt. %, of a silica sol is mixed with particulate silica. A useful particulate silica is a fumed silica such as Aerosil® (Degussa Chemical Company). A typical silica particulate material has a high surface area (about 200 $m^2/g$) with essentially no micropores, and, typically, are aggregates (with mean diameters of several hundred nm) of individual particles with average diameters of about 10 nm (above 7 nm). Preferably, the silica is sodium free. Sufficient particulate silica is added to the mixture to obtain a desired pore volume in the resulting support particle. The amount of particulate silica may range up to 90 wt. % and typically ranges up to 10 to 50 wt. % of the silica in the mixture. Typically, the silica sol/particulate silica mixture is spray dried at an elevated temperature such as between 115° to 280° C., preferably 130° to 240° C., followed by calcining at temperature typically ranging from between 550° to 700° and, preferably 630° to 660° C.

An advantageous silica sol for preparing a catalyst support useful in the present invention contains silica particles in the sol typically more than 20 nanometers in mean diameter and may be up to about 100 nanometers or more Preferable sols contain silica particles of about 40 to 80 nanometers. Nalco silica sol 1060 particularly is advantageous because of the relatively large mean silica particle sizes of 60 nm pack less efficiently than smaller sol particles such as Nalco 2327 at about 20 nm. The larger particle size sol yields a final support with higher mesopore volume and less micropore volume.

A suitable support material for use in a fixed bed vinyl acetate process may be spherical The support particles typically may have a diameter of 3 to 9 mm. Surface areas (measured by nitrogen BET) for fixed bed support particles with mean diameters and pore volumes useful in this invention typically are above about 5 $m^2/g$ and may range up to about 800 $m^2/g$. Suitably, a fixed bed support particle has a pore volume (measured by nitrogen sorption) between about 0.2 and 3.5 ml/gram. Suitably, fixed bed support particles have an apparent bulk density of 0.3 to 1.5 gram/ml.

Although silica-based support particles are the most preferred in this invention for use in fluid or fixed bed processes, other oxides may be used as long as a particle of appropriate size and with sufficient pore volume is produced in which may be deposited the required catalytic materials. Possible other oxides include alumina, silica-alumina, ceria, magnesia, titania, zirconia and mixed oxides and mixtures thereof. The support may be impregnated with organic or inorganic bases for example Group I or Group II hydroxides and ammonium hydroxide.

Preferably, the catalytically active metal comprises at least one Group VIII noble metal. The noble metals of Group VIII of the Periodic Table of the Elements (IUPAC) are palladium, platinum, rhodium, ruthenium, osmium and iridium. Typically, the noble metal used in a catalyst composition for the manufacture of vinyl acetate comprises palladium. Such a catalyst composition typically contains at least about 0.1%, preferably at least 0.2 wt % palladium to about 5 wt % and preferably up to 4 wt % palladium.

The catalytically active metal(s) may be impregnated in one or more steps onto the support particles in the form of precursor salt solutions. In a preferred aspect of the present invention, microspheroidal support particles are preferably impregnated with a palladium compound in a suitable solvent. Suitable solvents may be water, carboxylic acids such as acetic acid, benzene, toluene, alcohols such as methanol or ethanol, nitriles such as acetonitrile or benzonitrile, tetrahydrofuran or chlorinated solvents such as dichloromethane. Preferably, the solvent is water and/or acetic acid. Suitably, the support particles are impregnated with palladium acetate, sulphate, nitrate, chloride or halogen-containing palladium compounds such as $H_2PdCl_4$, which is sometimes also represented as $[PdCl_2]2HCl$, and Group I or Group II salts thereof such as $Na_2PdCl_4$ and $K_2PdCl_4$. A preferred water soluble compound is $Na_2PdCl_4$. A preferred acetic acid-soluble palladium compound is palladium acetate.

The catalyst composition suitable for the manufacture of vinyl acetate may also comprise, as promoters, other metals such as gold, copper, cerium and mixtures thereof preferably gold. These other metals may also be more concentrated in the layer than in the inner and outer regions, that is the inner and outer regions may have a lower concentration of said promoter metal than said layer Typically, the weight percent of gold is at least about 0.1 wt %, preferably, at least 0.2 wt % gold to about 3 wt % and preferably up to 1 wt % gold. Typically, the weight percent of cerium is at least about 0.1 wt %, preferably at least 0.2 wt % to about 10 wt % or more, preferably up to 5 wt % of cerium. Typically, the weight percent of copper is at least 0.1 to about 10 wt %, preferably up to 5 wt % copper.

Impregnation of the support particles with the gold, copper, cerium or mixtures thereof may be carried out together with or separately from the impregnation of the support particles with the Group VII noble metal compounds such as palladium compound(s). Suitable gold compounds include gold chloride, dimethyl gold acetate, barium acetoaurate, gold acetate, tetrachloroauric acid ($HAuCl_4$, sometimes represented as $AuCl_3.HCl$) and Group I and Group II salts of tetrachloroauric acid such as $NaAuCl_4$ and $KAuCl_4$. Preferably, the gold compound is $HAuCl_4$. The gold compounds may be prepared in situ from suitable reagents. These promoters may be used in an amount of 0.1 to 10% by weight of each promoter metal present in the finished catalyst composition.

In catalyst compositions suitable for the production of vinyl acetate, in addition to Group VIII noble metals such as palladium and optional promoter selected from gold, copper and cerium, the support particles may also be impregnated at any suitable stage during the preparation process with one or more salts of Group I, Group II, lanthanide and transition metals promoters, preferably of cadmium, barium, potassium, sodium, manganese, antimony, lanthanum or matures thereof, which are present in the finished catalyst composition as salts, typically acetates. Generally, potassium will be present. Suitable salts of these compounds are acetates but any soluble salt may be used. These promoters may be used in an amount of 0.1 to 15%, preferably 3 to 9%, by weight of each promoter salt present in the finished catalyst composition.

The impregnation of the support particles may be performed using any suitable technique. A preferable method to impregnate salt solutions is an incipient wetness technique in which there is used a salt solution in an amount up to the volume of the pores of the support particles without excess solution being used. Thus, a desired level of metal compounds such as palladium and other metal species may be incorporated into the support particles by calculating the amount of metals and the volume of solution needed. The impregnation is typically performed at ambient temperature. Elevated temperatures may be used for example, with palladium acetate in acetic acid, greater than 60° C. and up to 120° C.

The impregnated support particles may optionally be dried and the impregnation step repeated two or more times if there is required higher metal or promoter loadings, than the solubility of the salt in the solvent will allow. The drying step may be performed at up to 140° C., preferably up to 120° C. The drying step may be performed at ambient temperature and reduced pressure. Air, nitrogen, helium, carbon dioxide or any suitable inert gas may be used in the drying step. The catalyst composition may be tumbled, rotated or agitated by the gas stream or mechanical means to aid drying.

The impregnated support particles are preferably washed to remove anion contaminants, for example, nitrates, sulphates and usually halides. For chloride removal, washing with de-ionised water should proceed until a silver nitrate test shows that there is no soluble chloride present. The anion contamination levels should be minimised for the preparation of catalyst compositions suitable for the production of vinyl acetate. Cation contaminants should be minimised for the preparation of catalyst compositions for the production of vinyl acetate; for example to below 0.5 wt %, preferably below 0.2 wt % of sodium in the dried catalyst composition. Low levels of these contaminants are likely to remain; it is not essential that the levels are absolutely zero. On a commercial scale, batch washing may be used. To speed up the process, warm water may be used. Also, ion exchange solutions (such as potassium acetate) can be used to displace chloride and sodium. Also, the reagents used for the preparation can be selected to avoid the use of chloride and sodium, for example, potassium metasilicate instead of other Group I or Group II salts such as a sodium salt.

The support may be impregnated with base.

The chemical reagent used to deposit and immobilize the metal or its precursor may be added to the metal- or precursor-impregnated support particles before or after the optional washing step, depending on the reagents used. The chemical reagent may be a reducing agent such as hydrazine, formaldehyde, sodium formate, sodium borohydride, methanol or alcohols, preferably hydrazine. Hydrazine is preferably used as an aqueous solution. Gaseous reagents for example, hydrogen or hydrocarbons such as ethylene, may be used as alternative chemical reagents to deposit and immobilize the metal or its precursor.

It has been found that the amount of chemical reagent needed to give a layered structure depends on the amount of metal e.g. Group VIII noble metal such as palladium metal which is present in the catalyst composition. Generally, higher concentrations of chemical reagent than have hitherto been used are used. Thus, for example, if palladium is present in the catalyst composition in amounts of 0.5–2 wt %, a hydrazine concentration in water in excess of 2 wt %, for example, at least 3 wt %, such as 4–20 wt % and preferably 4–8 wt % has been found to produce a layered structure of the present invention. It has also been found that the more concentrated the solution of hydrazine the greater the distance the layer will be below the surface of the particle.

Typically, the chemical reagents such as aqueous hydrazine are used at ambient temperatures but temperatures up to 100° C. may be used. Typically, an excess of chemical reagent is used. The reagent will reduce the impregnated metal precursor species to catalytically active zero valence noble metal crystallites Preferably hydrazine at a concentration in water of at least 2 wt %, preferably in excess of 2 wt %, for example at least 4 wt %, is used in the preparation of the catalyst compositions. Thus, according to another embodiment of the present invention there is provided a process for preparing a catalyst composition wherein said process comprises impregnating support particles with a solution of least one Group VIII noble metal and then contacting the impregnated support with hydrazine at a concentration in water of at least 2 wt %.

Contacting the chemical reagent with the mobile metal- or precursor-impregnated support particles deposits and immobilizes the metal or its precursor such that the metal or its precursor is distributed as a layer below the surface of each support particle. Preferably, at least 50% of the metal is distributed as a layer in each support particle. The distribution of the metal may be determined by suitable techniques such as Electron Microscopy.

Base may be used to influence the mobility of the metal or its precursor and to affect the size and location of the layer. The base may be added before or during the impregnation of the support with the metal or its precursor. There should not be used so much base as to completely immobilize the metal or its precursor before addition of the chemical reagent.

The catalyst compositions of the present invention may be used in fixed or fluid bed reactors for the production of vinyl acetate, by the reaction of ethylene and acetic acid with molecular oxygen containing gas in the presence of the catalyst composition. Preferably, a fluid bed reactor is used to produce vinyl acetate under fluidised bed reaction conditions. The reaction temperature suitably is maintained at about 100° to 250° C., preferably 130° to 190° C. The reaction pressure suitably is about 50 to 200 psig (3 to 14 barg), preferably 75 to 150 psig (5 to 10 barg). In a fluid bed reactor system, the particles of the catalyst composition are maintained in a fluidized state by sufficient gas flow through the system. This gas flow preferably is maintained at a suitable level to maintain the fluidization. Excess flow rate may cause channeling of the gas through the reactor which decreases conversion efficiency. Additional alkali metal salt promoter may be added during the process to maintain activity.

BRIEF DESCRIPTION OF THE DRAWINGS

The invention will now be illustrated by reference to the following examples and drawings in which

In FIG. 1, a catalyst particle (I) is provided with a layer (2) of a Group VIII noble metal such as palladium. The layer (2) may optionally contain other metals such as gold. The layer (2) is located with an outer edge (7) below the particle surface (3) and between an inner region (4) and an outer region (5) of the catalyst particle having lower concentrations of the Group VIII noble metal and/or other metals than the layer (2).

FIG. 2 illustrates an X-ray profile from beyond and across a section of a catalyst particle containing palladium and gold using an Electron Microprobe Analyser, for example along line X–X' of FIG. 1. FIG. 2 clearly illustrates that the palladium and gold are both mainly distributed in two specific locations along the diameter of the particle (that is, as a layer below the surface of the particle) with lower concentrations of palladium and gold distributed elsewhere. In FIG. 2 the outer edges of the particle are at positions labeled A and A' at 0 and 97 microns.

EXAMPLES

Figure 1:
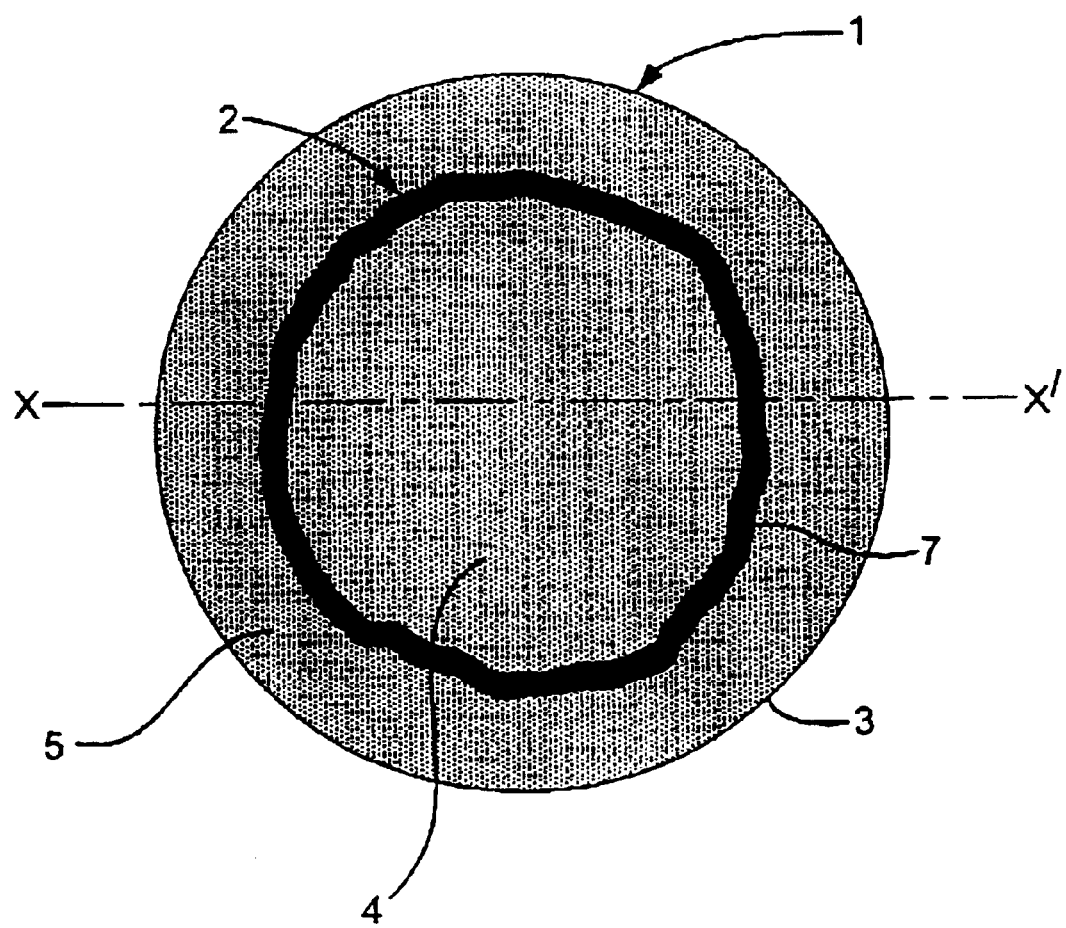
FIG. 1 illustrates a cross-section of a typical catalyst particle according to the present invention and FIG. 2 illustrates an X-ray profile through a section of a catalyst particle according to the present invention.
Figure 2:
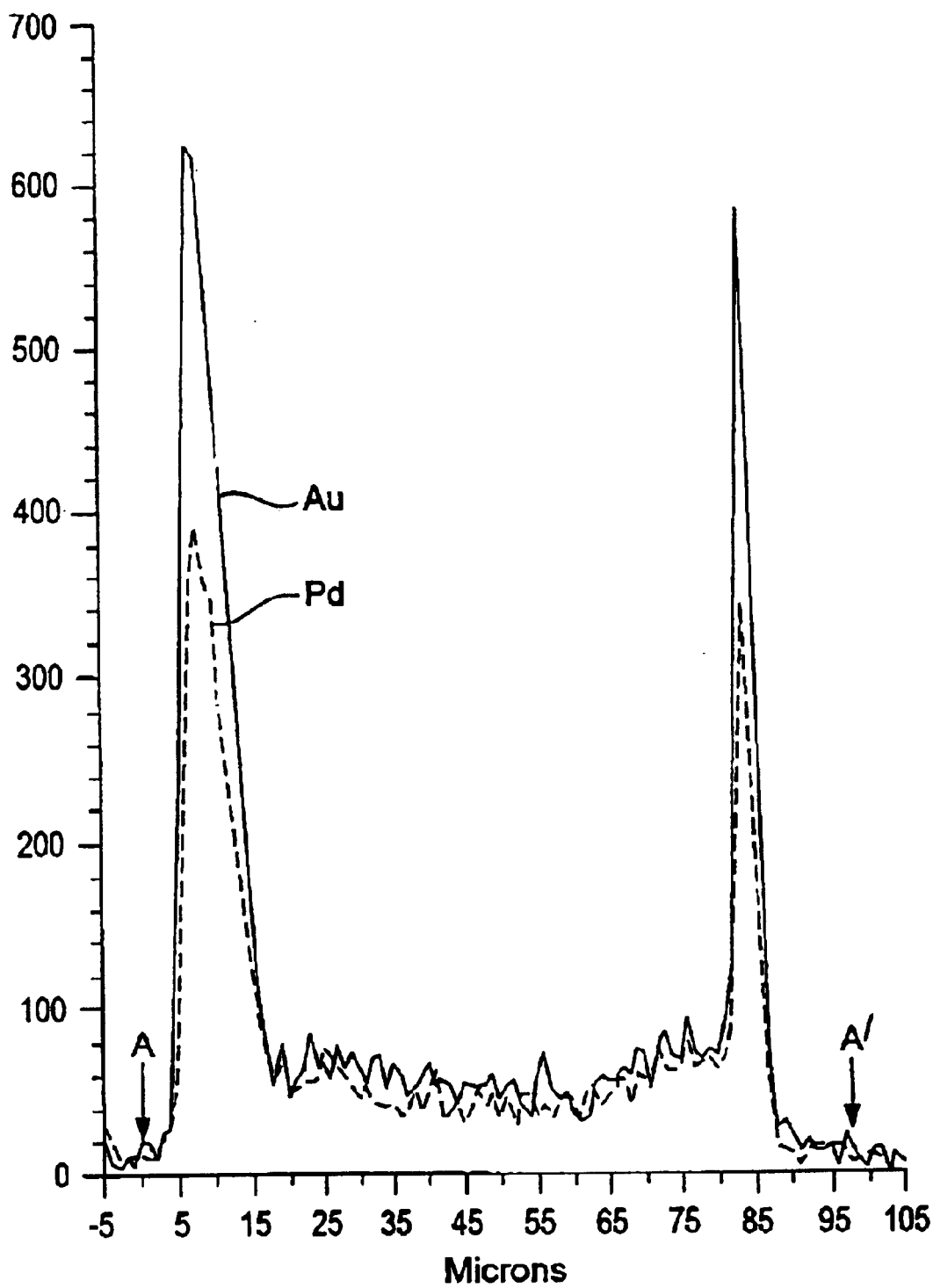

The following Examples illustrate but do not limit the invention described and claimed herein.
Preparation of the Support Particles
Preformed microspheroidal support particles comprising 100% silica were used for all the Examples described below.
The support particles were prepared by spray-drying a mixture of Nalco silica sol 1060 (Nalco Chemical Company) and Degussa Aerosil® silica (Degussa Chemical Company). In the dried support particles, 80% of the silica came from the sol and 20% of the silica came from the Aerosil. The spray-dried microspheroidal support particles were calcined in air at 640° C. for 4 hours. Prior to use the support particles were sieved and a specific particle size distribution was used in the preparation of the catalyst compositions as follows:

| Particle size | % |
|---|---|
| >300 microns | 2 |
| 88–300 microns | 30 |
| 44–88 microns | 38 |
| <44 microns | 30 |

Comparative Example 1 and Examples 2, 3 and 4

The following procedure describes the method of preparation of four fluid bed vinyl acetate catalyst compositions (1.6 wt % palladium, 0.7 wt % gold, 7 wt % potassium acetate on silica).
Preparation of Catalyst Compositions
Silica support particles (163 g) were impregnated with a solution of $Na_2PdCl_4 \cdot xH_2O$ (containing 2.9 g palladium) and $HAuCl_4 \cdot xH_2O$ (containing 1.2 g gold) in distilled water by incipient wetness. The resulting mixture was mixed thoroughly, left to stand for 1 hour and dried overnight.
A 35 g portion of the dried impregnated material was added slowly to each of a 1 wt % (Comparative Example 1), 2 wt %, 4 wt %, and 8 wt % (Examples 2–4) solution of hydrazine in distilled water at room temperature and the mixture was allowed to stand with occasional stirring. Thereafter the mixture was filtered, washed with distilled water and dried overnight.
The material was then impregnated with an aqueous solution of potassium acetate (2.6 g) by incipient wetness. The resulting mixture was mixed thoroughly, left to stand for 1 hour and dried overnight.

Comparative Example 5 and Example 6

The following procedure describes the method of preparation of fluid bed vinyl acetate catalyst compositions (1.6 wt % palladium, 0.7 wt % gold, 7 wt % potassium acetate on silica)
Preparation of Catalyst Compositions
Silica support particles (163 g) were impregnated with a solution of $Na_2PdCl_4 \cdot xH_2O$ (containing 2.9 g palladium) and $HAuCl_4 \cdot xH_2O$ (containing 1.2 g gold) in distilled water by incipient wetness. The resulting mixture was mixed thoroughly, left to stand for 1 hour and dried overnight.
A 35 g portion of the dried impregnated material was added slowly to each of a 1 wt % (Comparative Example 5) and 8 wt % (Example 6) solution of hydrazine in distilled water at 80° C. and the mixture was allowed to stand with occasional stirring. Thereafter the mixture was filtered, washed with distilled water and dried overnight.
The material was then impregnated with an aqueous solution of potassium acetate (2.6 g) by incipient wetness. The resulting mixture was mixed thoroughly, left to stand for 1 hour and dried overnight.

Example 7

The following procedure describes the method of preparation of a fluid bed vinyl acetate catalyst composition (1.0 wt % palladium, 0.4 wt % gold, 5 wt % potassium acetate on silica)
Preparation of Catalyst Composition
Silica support particles (468 parts by weight) were impregnated with a solution of $Na_2PdCl_4 \cdot xH_2O$ (containing 5.00 parts by weight palladium) and $HAuCl_4 \cdot xH_2O$ (containing 2.00 parts by weight gold) in distilled water by incipient wetness. The resulting mixture was mixed thoroughly and dried overnight.

The dried impregnated material was added slowly to a room temperature solution of hydrazine in distilled water (4 wt %), and the mixture was allowed to stand with occasional stirring. Thereafter the mixture was filtered, washed with distilled water.

The material was doped with solid potassium acetate (25.0 parts by weight). The resulting mixture was mixed thoroughly and dried overnight.

Measurement of Noble Metal Layer Depth

A sample (approx. 20 particles) from each of Comparative Examples 1 and 5 and Example 2–4 and 6–7 was set in Araldite® resin overnight at 60° C. Thin sections (<100 nm) were cut with a diamond knife from prepared 'mesas'. The images were recorded by Transmission Electron Microscopy (TEM) using a JEOL 2000FX instrument. Photographic plates of the catalyst composition particles were then studied and measurements of the depth of the major layer of metals from the particle surface were made. No measurements were made on any particle with a diameter of 25 microns or less. The results are given in Table 1.

TABLE 1

| Example | Hydrazine concentration (wt %) | Reduction temperature | Average layer depth below surface (microns) | Average layer thickness (microns) |
| --- | --- | --- | --- | --- |
| Comparative 1 | 1 | room temp. | 1 | 1 |
| 2 | 2 | room temp. | 3 | 0.75 |
| 3 | 4 | room temp. | 6 | 0.25 |
| 4 | 8 | room temp. | 8 | 0.25 |
| Comparative 5 | 1 | 80° C. | 1 | 1.5 |
| 6 | 8 | 80° C. | 10 | 0.5 |
| 7 | 4 | room temp. | 8 | 0.25 |

The data illustrates that as the hydrazine concentration increases the layer depth below the surface increases. This effect is observed at both room temperature and at 80° C. The greater the layer depth the more protected the noble metal catalyst component will be from loss by abrasion or attrition.

Example 8—Preparation of Catalyst Composition Without Gold

Silica support (47 g) was impregnated with a solution of $Na_2Pd_2Cl_4 \cdot xH_2O$ (containing 0.5 g palladium) in distilled water by incipient wetness. The resulting material was mixed thoroughly and thereafter dried overnight.

The dried impregnated material was added slowly to a stirred solution of hydrazine in distilled water (4 wt. %) and the mixture allowed to stand with occasional stirring. Thereafter the material was filtered and washed with distilled water.

The material was impregnated with an aqueous solution of potassium acetate (2.5 g) by incipient wetness. The resultant material was left to stand for 1 hour and dried overnight.

Examination of this material showed that it also had a layered structure but that the layer of palladium seas broader than in the catalyst materials of examples 2–4 and 6–7.

Metal Loss Experiment

Microspheroidal catalysts containing palladium and gold were subjected to attrition tests in a 38 mm internal diameter fluid bed test apparatus provided with a freeboard section and air feed through three 0.4 mm diameter nozzles with a gas velocity of 320 m/s. 50 g samples of catalyst were used in 20 hour tests which were designed to mimic attrition in a fluid bed reactor for the production of vinyl acetate from ethylene, acetic acid and oxygen, but under accelerated conditions. The freeboard section of the apparatus enabled the bulk of the catalyst to be retained in the vessel during the experiment, but fines formed by attrition escaped from the top of the vessel and were collected in filters and measured. The metal content of the recovered fines was measured and expressed as a percentage of the metal in the catalyst. This provided a measure of the attrition.

Catalyst A was a shell type catalyst whereas catalyst B had been prepared by a process according to the present invention. A significant proportion of the palladium and gold in catalyst B was located in a layer with an outer edge 8 microns below the surface of the particles.

Table 2 shows the amounts of palladium and gold lost by the two catalysts during the attrition test.

TABLE 2

| Catalyst | palladium loss | gold loss |
| --- | --- | --- |
| A | 56.0% | 52.2% |
| B | 4.0% | 5.9% |

The results in table 2 show that the catalyst according to the present invention loses less of the catalytically active metals palladium and gold than the shell type catalyst.

We claim:

1. A process for preparing a supported metal catalyst composition comprising:
    impregnating support particles having a mean diameter of greater than 300 microns with a solution of least one catalytically active metal, or precursor thereof, such that the metal, or its precursor, is in a mobile state in the support particles; and
    drying the impregnated support particles and then treating the mobile metal, or its precursor, in the support particles with a liquid comprising at least one reducing agent to deposit and immobilize the metal, or its precursor, in the support particles such that the metal, or its precursor, is distributed in the support particle in a layer below the surface of said support particle, said layer being between an inner and an outer region, each of said inner and outer regions having a lower concentration of said metal or precursor than said layer.

2. A process as claimed in claim 1, wherein the catalytically active metal comprises at least one Group VIII noble metal.

3. A process as claimed in claim 2, wherein the Group VIII noble metal comprises palladium.

4. A process as claimed in claim 3, wherein palladium is present in the catalyst composition in an amount of 0.5–2 wt %, and the concentration of reducing agent in the liquid is in excess of a molar equivalent of 2 wt % hydrazine concentration.

5. A process as claimed in claim 4, wherein the concentration of reducing agent in the liquid is at least a molar equivalent of 3 wt % hydrazine.

6. A process as claimed in claim 5, wherein the concentration of reducing agent in the liquid is a molar equivalent of 4–20 wt % hydrazine.

7. A process as claimed in claim 6, wherein the concentration of reducing agent in the liquid is a molar equivalent of 4–8 wt % hydrazine.

8. A process as claimed in claim 2, wherein the Group VIII metal comprises palladium; and the support is impregnated with at least one other promoter selected from the group consisting of gold, copper, cerium and mixtures thereof; and at least one promoter selected from the group consisting of salts of Group I, Group II, lanthanide and transition metals.

9. A process as claimed in claim 8, wherein said inner and outer regions have a lower concentration of said promoter metal selected from the group consisting of gold, copper, cerium and mixtures thereof than said layer.

10. A process as claimed in claim 1, wherein the reducing agent is selected from the group consisting of hydrazine, formaldehyde, sodium formate, sodium borohydride, and alcohols.

11. A process as claimed in claim 1, wherein the support is impregnated with base.

12. A process as claimed in claim 1, wherein the layer containing the catalytically active metal or precursor thereof has an outer edge which is at least 3% and no more than 75% of the particle radius from the surface of the support particle.

13. A process as claimed in claim 12, wherein the layer has an average thickness of less than half the radius of the particle.

14. A process as claimed in claim 12, wherein the layer containing the catalytically active metal or precursor thereof has an outer edge which is at least 5% of the particle radius from the surface of the support particle.

15. A process as claimed in claim 14, wherein the layer containing the catalytically active metal or precursor thereof has an outer edge which is at least 10% of the particle radius from the surface of the support particle.

16. A process as claimed in claim 1, wherein the layer containing the catalytically active metal or precursor thereof has an outer edge which is at least 3 microns and no more than 20 microns below the surface of each support particle.

17. A process as claimed in claim 16, wherein the layer containing the catalytically active metal or precursor thereof has an outer edge which is 4 to 20 microns below the surface of each support particle.

18. A process as claimed in claim 17, wherein the layer containing the catalytically active metal or precursor thereof has an outer edge which is 5 to 15 microns below the surface of each support particle.

19. A process as claimed in claim 1, wherein the layer has an average thickness of less than half the radius of the particle.

20. A process as claimed in claim 1, wherein the layer has an average thickness of greater than 0.1 microns.

21. A process as claimed in claim 20, wherein the layer has an average thickness of greater than 0.1 microns and less than 25 microns.

22. A process for preparation of vinyl acetate comprising reacting ethylene and acetic acid with molecular oxygen containing gas in the presence of a catalyst composition prepared by a process as claimed in claim 1.

23. A process as claimed in claim 22, wherein a fluidized bed reactor is used for conducting the reaction.

* * * * *